United States Patent
Schermer et al.

(10) Patent No.: US 6,447,723 B1
(45) Date of Patent: Sep. 10, 2002

(54) MICROARRAY SPOTTING INSTRUMENTS INCORPORATING SENSORS AND METHODS OF USING SENSORS FOR IMPROVING PERFORMANCE OF MICROARRAY SPOTTING INSTRUMENTS

(75) Inventors: Mack J. Schermer, Belmont, MA (US); Mona L. Phaff, Winchester, MA (US)

(73) Assignee: Packard Instrument Company, Inc., Meriden, CT (US)

( * ) Notice: Subject to any disclaimer, the term of this patent is extended or adjusted under 35 U.S.C. 154(b) by 0 days.

(21) Appl. No.: 09/524,657

(22) Filed: Mar. 13, 2000

(51) Int. Cl.[7] .............................................. G01N 35/00
(52) U.S. Cl. ................. 422/62; 422/63; 422/82.05; 422/100; 422/104; 436/43; 436/180; 382/129
(58) Field of Search ............................... 210/91; 422/62, 422/63, 68.1, 82.05, 82.06, 82.07, 82.08, 81, 100, 104; 436/43, 48, 174, 180, 501, 518; 435/6; 382/128, 129, 133

(56) References Cited

U.S. PATENT DOCUMENTS

| | | |
|---|---|---|
| 4,817,443 A | 4/1989 | Champseix et al. |
| 5,055,263 A | 10/1991 | Meltzer |
| 5,133,373 A | 7/1992 | Hoffman et al. |
| 5,306,510 A | 4/1994 | Meltzer |
| 5,408,891 A | 4/1995 | Barber et al. |
| 5,411,065 A | 5/1995 | Meador et al. ............... 141/1 |
| 5,474,744 A | 12/1995 | Lerch |
| 5,525,515 A | 6/1996 | Blattner |
| 5,603,342 A | 2/1997 | Shambaugh |
| 5,700,637 A | 12/1997 | Southern |
| 5,770,151 A | 6/1998 | Roach et al. |
| 5,798,035 A * | 8/1998 | Kirk et al. .................... 422/63 |
| 5,807,522 A | 9/1998 | Brown et al. |
| 5,827,744 A | 10/1998 | Fose et al. |
| 5,847,105 A | 12/1998 | Baldeschwieler et al. |
| 5,895,915 A | 4/1999 | DeWeerd et al. |
| 5,897,837 A | 4/1999 | Mizuno |
| 5,922,617 A | 7/1999 | Wang et al. |

(List continued on next page.)

FOREIGN PATENT DOCUMENTS

| | | |
|---|---|---|
| EP | 0 287 783 | 10/1988 |
| GB | 2 310 006 A | 8/1997 |
| WO | WO 99/22867 | 5/1999 |
| WO | WO 99/34931 | 7/1999 |
| WO | WO 99/36760 | 7/1999 |
| WO | WO 99/42804 | 8/1999 |
| WO | WO 00/01798 | 1/2000 |
| WO | WO 00/13796 | 3/2000 |
| WO | WO 00/51058 | 8/2000 |
| WO | WO 00/63705 | 10/2000 |
| WO | WO 01/58593 | 8/2001 |

OTHER PUBLICATIONS

Website (WWW.intelligentbio.com) literature of Intelligent Bio–Instruments showing specifications of HT Production Microarrayer printed on Apr. 14, 2000.

(List continued on next page.)

Primary Examiner—Joseph W. Drodge
(74) Attorney, Agent, or Firm—Hale & Dorr LLP (57) ABSTRACT

The disclosed spotting instrument includes one or more sensors that are mechanically fixed to the instrument's printhead. The sensors enable the instrument to detect whether a substrate is mounted in a particular holder of the instrument's substrate station prior to attempting to print spots onto that substrate. Similarly, the sensors enable the instrument to detect whether a reservoir is mounted in a particular holder of the instrument's well station prior to attempting to collect a sample of target material from that reservoir. The sensors also enable the instrument to read bar code labels affixed to substrates or reservoirs mounted in the instrument.

18 Claims, 6 Drawing Sheets

U.S. PATENT DOCUMENTS

| | | | |
|---|---|---|---|
| 5,927,547 A | 7/1999 | Papen et al. | |
| 5,935,859 A | 8/1999 | Elliott et al. | |
| 5,957,167 A | 9/1999 | Feygin | |
| 6,015,880 A | 1/2000 | Baldeschwieler et al. | |
| 6,017,496 A | 1/2000 | Nova et al. | |
| 6,024,925 A | 2/2000 | Little et al. | 422/100 |
| 6,039,211 A | 3/2000 | Slater et al. | 222/1 |
| 6,083,763 A * | 7/2000 | Balch | 436/518 |
| 6,101,946 A | 8/2000 | Martinsky | |
| 6,187,267 B1 * | 2/2001 | Taylor et al. | 422/82.05 |
| 6,215,894 B1 | 4/2001 | Zeleny et al. | |
| 6,323,043 B1 * | 11/2001 | Caren et al. | 436/518 |
| 6,362,004 B1 * | 3/2002 | Noblett | 436/43 |

OTHER PUBLICATIONS

Website (www.Labman.co.uk) literature of Labman Automation Limited showing specifications of Microarray Spotter systems printed on Apr. 14, 2000.

Mark Schena (editor), "Microarray Biochip Technology", Chapter 2, pp 19–38 (relevant pp. 33–36 entitled *Pin Washing and Sample Carryover*), Eaton Publishing, BioTechniques Books Division, Natick, Massachusetts U.S.A., Undated.

Alexander Kuklin, Ph.D., "Automation Microarray Image Processing And Data Mining, High Throughput Screening" (Supplement to Biomedical Products), Jan. 2000, pp. 4, 5, 6, 8, Cahners Publishing, Morris Plains, New Jersey, U.S.A.

Mark Schena, "DNA Microarrays: A Practical Approach", Chapters 2 and 6 (pp. 17–42 and pp. 101–120), New York, Oxford University Press, 1999, ISBN 0–19–963776–8.

GSI Lumonics ScanArray Technical Note 300: ScanArray Microarray Barcodes: Automated Microarray Analysis & Data Tracking, Jun. 1999.

Website (www.biorobotics.co.uk) literature of BioRobotics, Inc. showing specifications of MicroGrid printed Jan. 14, 2000.

Website (www.cartesiantech.com) literature of Cartesian Technologies showing specifications of PinArray, nQUAD, CloneTracker and PegaSys printed Jan. 14, 2000.

Website (www.genemachines.com) literature of GeneMachines showing specifications of OmniGrid printed Jan. 14, 2000.

Website (www.geneticmicro.com) literature of Genetic MicroSystems, Inc. showing specifications of GMS Microarray Analysis System printed on Jan. 14, 2000.

Website (www.genetix.co.uk) literature of Genetix Limited showing specifications of Q Array MicroArrayer printed Jan. 14, 2000.

Website (www.genpakdna.com) literature of GenPak, Inc. showing specifications of genpak Array 21 Robotic Micro–Arrayer System printed on Jan. 14, 2000.

Website (www.genomicsolutions.com) literature of Genomic Solutions, Inc. showing specifications of Flexys printed on Jan. 14, 2000.

Website (www.esit.com) literature of Engineering Services Inc. showing specifications of SDDC printed on Jan. 14, 2000.

Website (www.packardinst.com) literature of Packard Instrument Company showing specifications of The Bio-Chip Arrayer printed on Jan. 17, 2000.

Website (www.arrayit.com) literature of TeleChem International, Inc. showing specifications of ArrayIt printed on Jan. 14, 2000.

Website (www.majerprecision.com) literature of Majer Precision Engineering showing specifications of MicroQuill printed on Jan. 14, 2000.

Website (www.corning.com) literature of Corning Incorporated showing specifications of Corning Microarray Technology (CMT) printed on Jan. 27, 2000.

Website (http://nunc.nalgenunc.com) literature of Nalge Nunc International showing specifications of MicroWell Plates printed Jan. 27, 2000.

Website (www.keyence.com) literature of Keyence Corporation of America showing specifications of CCD Bar Code Readers, undated.

Genetic MicroSystems Product Literature of GMS Microarray Analysis System, undated.

Website (www.sharpmeg.com) literature of Sharp Microelectronics of the Americas showing specifications of Optoelectronic Devices printed on Jan. 28, 2000.

Sharp Product Literature of GP2A20/GP2A22 printed at least as early as Jan. 28, 2000.

Sharp Product Literature of GP2A111 printed at least as early as Jan. 28, 2000.

Anonymous, "Wire Printer Diagnostic Method," IBM Technical Disclosure Bulletin, vol. 27, No. 9, 1985, p 5042.

"Patent Abstracts of Japan," vol. 007, No. 196, Aug 26, 1983.

Derisi et al, "The Mguide, a Complete Guide to Building Your own Microarrayer," Biochemistry Department of Stanford University, 1999, pp 19–20.

Rose, "Application of a Novel Microarraying System in Genomics Research and Drug Discovery," Journal of the Association for Laboratory Automation, vol. 3, No. 3, Jul. 1998, pp 53–56.

Schummer et al., "Inexpensive Handheld Device for the Construction of High–Density Nucleic Acid Arrays," BioTechniques, vol. 23, No. 6, 1997, pp 1087–1090.

Patent Abstracts of Japan: Kogyo, "Transcribing Member for Liquid and its Device," Publication No. 2000287670 (17–10–00).

* cited by examiner

MICROARRAY SPOTTING INSTRUMENTS INCORPORATING SENSORS AND METHODS OF USING SENSORS FOR IMPROVING PERFORMANCE OF MICROARRAY SPOTTING INSTRUMENTS

BACKGROUND OF THE INVENTION

The present invention relates to microarray spotting instruments. More particularly, the present invention relates to improved spotting instruments that incorporate sensors and methods of using those sensors for improving performance of the spotting instruments.

As is well known (and described for example in U.S. Pat. No. 5,807,522 to Brown et al. and in "DNA Microarrays: A Practical Approach", Schena, Mark, New York, Oxford University Press, 1999, ISBN 0-19-963776-8), microarrays are arrays of very small samples of purified DNA or protein target material arranged as a grid of hundreds or thousands of small spots on a solid substrate. When the microarray is exposed to selected probe material, the probe material selectively binds to the target spots only where complementary bonding sites occur, through a process called hybridization. Subsequent quantitative scanning by a fluorescent microarray scanner (i.e., a scanning instrument) may be used to produce a pixel map of fluorescent intensities (See, e.g., U.S. Pat. No. 5,895,915, to DeWeerd et al.). This fluorescent intensity map can then be analyzed by special purpose quantitation algorithms which reveal the relative concentrations of the fluorescent probes and hence the level of gene expression, protein concentration, etc., present in the cells from which the probe samples were extracted.

The microarray substrate is generally made of glass which has been treated chemically to provide for molecular attachment of the spot samples of microarray target material. The microarray substrate is also generally of the same size and shape as a standard microscope slide, about 25 mm×75 mm×1 mm thick. The array area can extend to within about 1.5 mm of the edges of the substrate, or can be smaller. The spots of target material (typically DNA) are approximately round. The spot diameter is generally determined by the dispensing or spotting technique used and typically varies from about 75 microns to about 500 microns, and may be as small as about 20 microns. The general trend is toward smaller spots, which produce more compact arrays. The center-to-center spacing between the spots usually falls into the range of 1.5 to 2.5 spot diameters.

Figure 1A:
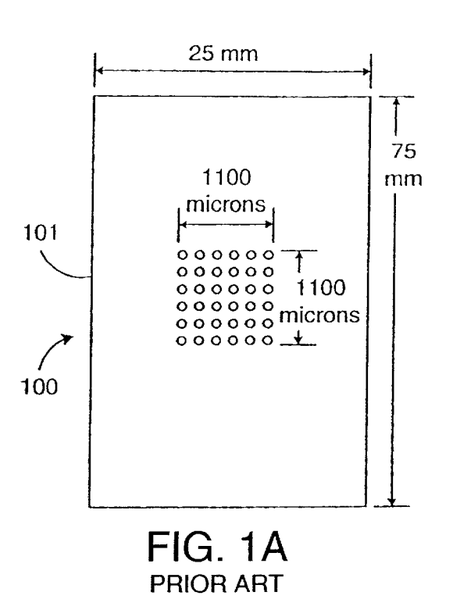
FIG. 1A shows a top view of a prior art microarray.

FIG. 1A, which is not drawn to scale, shows a top view of a prior art microarray 100. In FIG. 1A, each of the circles represents a tiny spot of target material that has been deposited onto a rectangular glass substrate 101, and the spots are shown in a magnified view as compared to the substrate 101. Assuming typical dimensions of 100 μm spot diameter and 200 μm center-to-center spacing between the spots, the illustrated six by six array of spots covers only a 1100 μm by 1100 μm square area of the 25 mm by 75 mm area defined by the substrate 101. Thousands of spots are usually deposited in a typical microarray and the spots may cover nearly the entire substrate. The portion of the microarray that is covered with spots of target material may be referred to as the "active area" of the microarray.

Figure 1B:
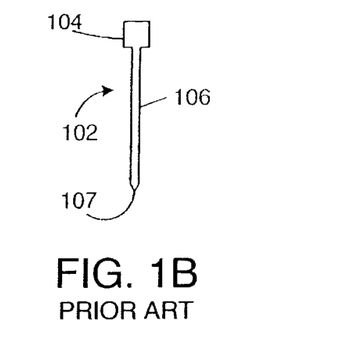
FIG. 1B shows a side view of a prior art pin.

There are several well known methods of depositing the spots onto the substrate of a microarray, and instruments that deposit the spots are typically referred to as "spotting instruments". One popular method is to use one or more "pins" to transfer the target material from a reservoir onto the microarray substrate. FIG. 1B shows an example of such a prior art pin 102, which includes a pin head 104 and a shaft 106. Both the pin head 104 and the shaft 106 are generally cylindrical, and the pin head 104 and shaft 106 are generally disposed so that they are coaxial. The diameter of the pin head 104 is greater than the diameter of the shaft 106, and the shaft is substantially longer than the pin. One end 107 of the shaft 106 is tapered or sharpened, and the other end of the shaft is attached or bonded to the pin head 104. Examples of such pins are described in, for example, U.S. Pat. No. 5,770,151 (Roach et al.) and U.S. Pat No. 5,807,522 (Brown et al.).

In operation, the sharp ends 107 of the pins are dipped into a reservoir of the liquid target material so that some of the material is "collected by" or becomes attached to the pins. The sharp ends of the pins are then placed in contact with the substrate to deposit tiny amounts of the material onto selected locations of the substrate. The pins are normally moved by a mechanical or robotic apparatus so the spots may be accurately placed at desired locations on the substrate.

Some types of pins are capable of collecting only enough target material to form a single spot on the microarray before they need to be re-dipped in the reservoir, whereas others can collect enough target material from the reservoir to form several or even hundreds of spots before they need to be re-dipped in the reservoir. In either case, the pins must be manufactured to very precise tolerances to insure that each spot formed by the pin will be of controlled size. As a result of these demanding specifications, the pins are rather expensive (e.g., a single pin typically costs several hundred dollars). Also, the sharp ends of the pins are so small and precisely shaped (e.g., a square tip measuring 50 microns on a side) that the pins are fragile. Accordingly, to prevent damage, the sharp ends of the pins should only be subjected to a tiny force when the sharp ends are placed in contact with the substrate or any other solid object.

Spotting instruments typically form microarrays in batches. For example, in a single "run", a spotting instrument may form up to one hundred identical microarrays. After forming enough spots of a particular target material to complete the batch of microarrays being spotted, the pins generally need to be washed (to remove any excess liquid target material), and then dried before they can be dipped into another reservoir of target material. So the process of forming microarrays with a "pin-type" spotting instrument includes steps of (1) positioning a pin over a reservoir of target material; (2) dipping the sharp end of the pin into the reservoir; (3) withdrawing the sharp end of the pin from the reservoir; (4) moving the pin over a selected location within the active area of a microarray; (5) lowering the pin to bring the sharp end of the pin into contact with the microarray substrate to form a single spot of controlled size at the selected location; (6) raising the pin to separate the sharp end of the pin from the substrate; (7) repeating steps (4), (5), and (6) until the pin's supply of target material is exhausted or until the desired number of spots have been placed on the bach of microarrays being produced; (8) washing the pin by either placing the pin in a stream of cleaning solution or by dipping the pin into a reservoir of cleaning solution; and (9) drying the pin. The spotting instrument repeats all of these steps numerous times to form a single microarray.

Figure 1C:
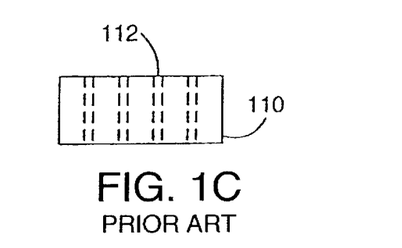
FIGS. 1C, 1D, and 1E show side, top, and perspective views, respectively, of a prior art printhead.
Figure 1D:
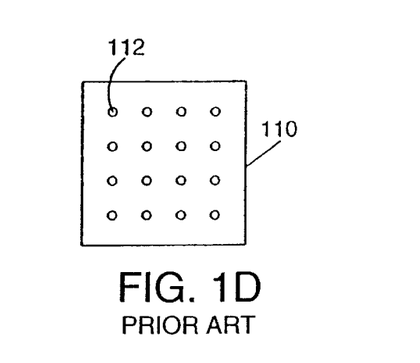
Figure 1E:
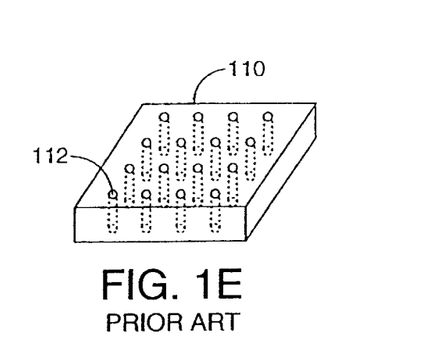
Figure 1F:
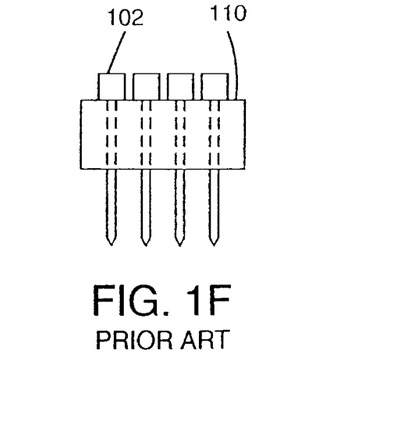
FIGS. 1F and 1G show side and top views, respectively, of sixteen pins mounted in the printhead shown in FIGS. 1C, 1D, and 1E.
Figure 1G:
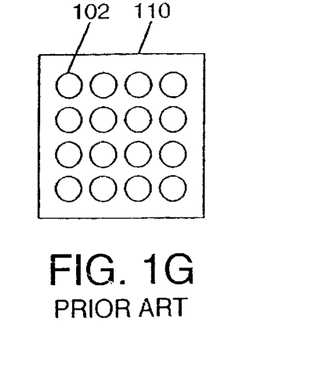

Since microarrays typically include thousands of spots, using only a single pin to form the microarray would be extremely time consuming. Accordingly, spotting instruments are often capable of simultaneously manipulating several pins. FIGS. 1C, 1D, and 1E show side, top, and perspective, views respectively of a printhead 110 that can simultaneously hold sixteen pins 102. Printhead 110 is a solid block of material, typically metal, that defines an array of sixteen apertures 112. The apertures 112 are slightly larger than the outer diameter of the shafts 106 so the shafts can extend through the apertures 112. The apertures 112 are also smaller than the outer diameter of the pin heads 104 so that when the shaft of a pin is dropped into one of the apertures 112, the pin head 104 will be supported by the upper surface of the printhead 110. The pins are thereby "slip-fit" into the apertures of the printhead. FIGS. 1F and 1G show side and top views, respectively, of sixteen pins mounted into printhead 110.

Figure 1H:
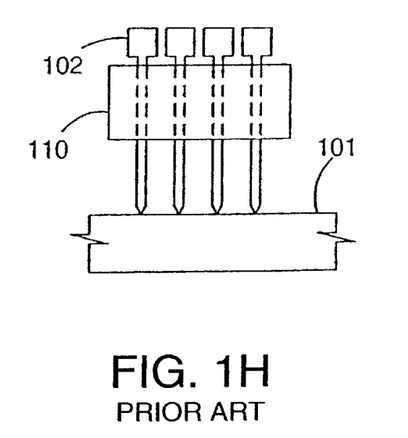
FIG. 1H shows a printing in which the printhead shown in FIG. 1F is lowered sufficiently with respect to a substrate to bring the sixteen pins shown in FIG. 1F into contact with the substrate and thereby form 16 spots of a microarray.

FIG. 1H illustrates printhead 110 being lowered to place the sharp ends of the pins 102 into contact with substrate 101 and thereby simultaneously forming sixteen spots of target material on the substrate. As shown, the printhead is generally lowered about 1 mm further than required to place the sharp ends of the pins in contact with the substrate. The slip-fit allows the upper surface of the printhead to be lowered beneath the bottom of the pin heads without imparting significant force to the sharp ends of the pins. The printhead is preferably lowered sufficiently slowly so that the force applied to the sharp ends of the pins (1) is principally determined by the weight of the pin plus a minor additional force due to the friction of the slip-fit and (2) is not significantly affected by inertial forces.

Figure 1I:
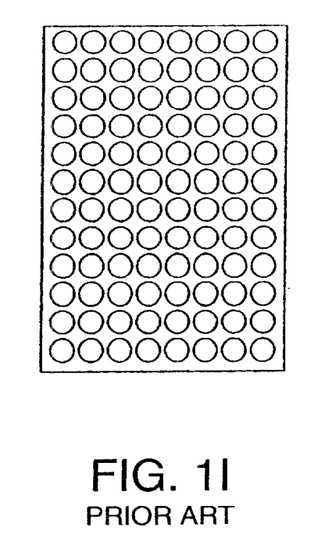
FIG. 1I shows a top view of a prior art 96-well plate.

Commercially available printheads provide between 4 and 72 apertures, thereby accommodating between 4 and 72 pins. Commercially available reservoirs provide a plurality of wells, or individual reservoirs, and permit each pin mounted in a printhead to be dipped into a separate well. Two popular reservoirs useful for producing microarrays are the "96-well plate" and the "384-well plate". Each of these plates provides a rectangular array of wells, each well being capable of holding a unique sample of liquid target material. FIG. 1I shows a top view of a 96-well plate. In 96-well plates, the centers of the individual reservoirs are separated by 9.0 mm, and in 384-well plates, the centers of the individual reservoirs are separated by 4.5 mm. The centers of adjacent apertures in commercially available printheads are correspondingly separated by either 9.0 or 4.5 mm.

Jets or nozzles, similar to those used for placing ink onto paper in ink-jet type printers, are another popular device used for forming spots on microarrays. Instead of using pins, jet type spotting instruments use one or more jets to form the spots on the microarray substrate. Each jet generally includes a hollow tube or needle and one end of the tube is configured as a nozzle. Initially, the nozzles are positioned over a reservoir and a vacuum is used to aspirate or collect a few microliters of target material into each of the hollow tubes. The nozzles are then positioned over a microarray substrate and a pulse of pressure applied to the tubes causes each tube to dispense a small amount of target material onto the substrate thereby forming a group of spots. Jet type spotting instruments are similar to pin type instruments. The principal difference is that in jet type instruments, the printhead carries an array of jets instead of an array of pins. In most respects, operation of the two types of instruments is similar.

In general, spotting instruments include mechanisms for holding or manipulating one or more plates (e.g., either 96-well or 384-well), a printhead (e.g., of either the pin-type or the jet-type), a robotic manipulator for controlling the movement of the printhead, mechanisms for holding a plurality of substrates, a pin or jet washer, and a dryer. The act of using a spotting instrument to form spots on a microarray substrate may be referred to as "printing".

Figure 2:
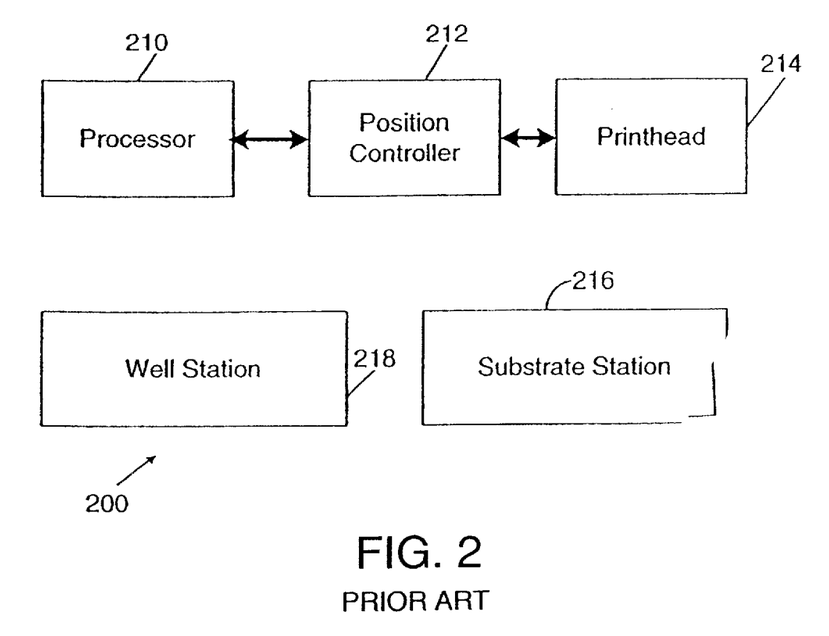
FIG. 2 shows a block diagram of a prior art spotting instrument.

FIG. 2 shows a block diagram illustrating a prior art spotting instrument 200. Instrument 200 includes a processor 210, a position controller 212, a printhead 214, a substrate station 216, and a well station 218. Although not illustrated, it will be appreciated that spotting instrument 200 may additionally include items such as a pin washer and a dryer (or a jet washer and dryer). Printhead 214 may be of the pin-type (i.e., one that holds one or more pins) or of the jet-type (i.e., one that holds one or more jets). Substrate station 216 generally includes platforms or holders for holding several (e.g., one hundred) microarray substrates and may further including a substrate handling system for automatically loading and unloading the substrates. Similarly, well station 218 generally includes platforms or holders for holding several reservoirs of target material (e.g., 96-well or 384-well plates) and may further include a handling system for automatically loading and unloading the reservoirs.

In operation, the processor 210 directs the position controller 212 (which is typically implemented as a robotic manipulator) to place the printhead 214 over one of the reservoirs stored in the well station 218 so that the printhead 214 may collect samples of selected target material. The processor then directs the position controller 212 and printhead 214 so as to print spots of the target material on one or more of the substrates being held in the substrate station 216. After all desired printing of that target material, the printhead may be cleaned and then placed over a different reservoir in the well station 218 to collect samples of some other target material. During printing of a batch of microarrays, it may be necessary to replace some of the reservoirs in the well station 218 with reservoirs containing different samples of target material.

For an experiment with a microarray to be useful, it is important to know the type of target material that was used to print every spot on the microarray. This can be extremely difficult for several reasons. For example, there are typically thousands of spots on a single microarray, and all spots tend to look alike. This makes it difficult to distinguish one spot from another on a single microarray and also makes it difficult to distinguish one microarray from another. Also, there is generally no easily discernable relationship between the location of a particular target material on a microarray (i.e., the location of spots printed using a particular target material) and the location of that target material in one or more of the reservoirs. This is because, for example, spots of different target material are typically printed next to one another and because multiple plates are typically used to form a single microarray.

Several attempts have been made in the prior art to facilitate use of microarrays and to make it easier to discern the type of target material used to form any given spot. For example, bar code labels have been included on the top of microarray substrates. Since the active area of a microarray often covers nearly the entire substrate, such labels are generally extremely small (e.g., 0.9 inches by 0.55 inches), and high-resolution bar code readers are required to read the labels. However, some microarray scanning instruments incorporate such bar code readers and this makes it easier to distinguish one microarray from another.

Another attempt to facilitate use of microarrays has been the inclusion of bar code labels on reservoirs of target material. Some prior art spotting instruments include a fixed bar code reader for reading the labels on the reservoirs. For example, in instrument 200 the well station 218 may include a fixed bar code reader for reading labels on reservoirs as they are moved by the well station's handling system. Since there is only limited space available on the top of a typical reservoir or plate for placing a bar code label, a convention or standard has developed of placing bar code labels on the sides of plates. In accordance with this convention, spotting instruments that include a bar code reader orient the reader so that it is "sideways looking", or so that light emitted from the reader travels in a direction that is parallel to the ground and perpendicular to the vertical sides of plates. Such fixed, sideways looking, bar code readers are capable of reading bar code labels that are affixed to the sides of the plates in accordance with the prior art convention.

Yet another attempt to facilitate use of microarrays has been the creation of software that allows an operator to specify general characteristics of a desired microarray and that uses those general specifications to generate control signals for controlling a spotting instrument so as to create the desired microarray. For example, such software allows the operator to specify (1) the desired configuration of the spots of a microarray (e.g., the number spots for the microarray, the location of each spot, and the type of target material that should be used for each spot); (2) the number of pins or jets to be used in the printhead; (3) the number and location of plates that will hold all samples of the target material; and (4) the identity of the target material located in each of the wells of each of the plates. The software then uses these general specifications to direct the spotting instrument to form a microarray, or a batch of microarrays, having the desired configuration of spots.

Despite these attempts, there remain significant problems with making and using microarrays. For example, prior art spotting instruments generally rely upon a human operator to verify that the necessary reservoirs or plates are accurately positioned within the instrument's well station and that substrates are properly mounted in all the holders of the substrate station. If the human operator makes any errors in this regard, the spotting instrument may become damaged or the microarrays may be incorrectly fabricated (e.g., incorrect target material may be used to form some of the spots on the microarrays). The job of the human operator is further complicated because a single "run" of a spotting instrument for producing a batch of microarrays generally takes several hours (e.g., twenty hours is a typical figure). Also, during a run, some of the plates must typically be removed from the instrument's well station and other plates must be added to the well station. If the human operator fails to make these substitutions at the correct times, or fails to notice changes in conditions of the instrument (e.g., a substrate that may have inadvertently become dislodged from one of the holders in the substrate station), the run may be delayed, the spotting instrument may suffer damage, or the run may be wasted since the microarrays may be fabricated incorrectly. The sideways looking bar code readers that have been incorporated into some prior art spotting instruments make the human operator's job a little easier. However, these bar code readers only inspect the plates while they are in the instrument's handling system and are not capable of determining whether the plates have been correctly loaded into the holders of the well station, nor do they identify the individual microarray substrates as having been spotted with a particular spotting protocol. Such information would be of value for data tracking and automated operation of downstream microarray processes such as application of probe, hybridization, scanning, quantification, etc.

It would therefore be advantageous to provide methods and apparatus for reducing the need for human supervision of spotting instruments.

SUMMARY OF THE INVENTION

These and other objects are provided by incorporating one or more sensors into a spotting instrument. The sensors are preferably mechanically fixed to the printhead and enable the spotting instrument to detect the presence or absence of substrates and/or wells in the spotting instrument.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE FIGURES

For a fuller understanding of the nature and objects of the present invention, reference should be made to the following detailed description taken in connection with the accompanying drawings in which the same reference numerals are used to indicate the same or similar parts wherein.

DETAILED DESCRIPTION OF THE PREFERRED EMBODIMENTS

Figure 3:
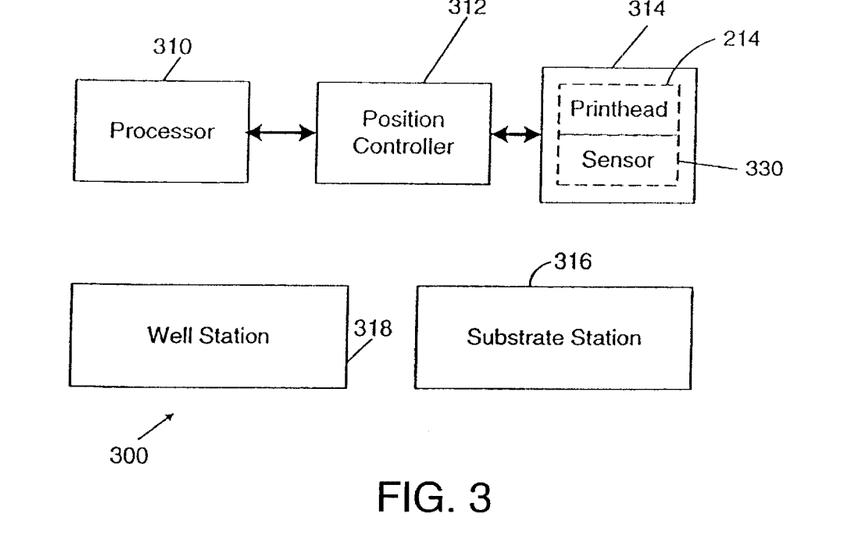
FIG. 3 shows a block diagram of a spotting instrument constructed according to the invention.

FIG. 3 shows a block diagram of a spotting instrument 300 constructed according to the invention. Instrument 300 includes a processor 310, a position controller 312, printhead-sensor 314, a substrate station 316, and a well station 318. Printhead-sensor 314 includes a prior art printhead (e.g., of the pin-type or jet-type) 214 and a sensor 330. Sensor 330 is capable of detecting (1) the presence or absence of reservoirs in well station 318; (2) the type of reservoirs located within well station 318; (3) the presence or absence of substrates in substrate station 216; and (4) the type of substrates located in substrate station 216. Sensor 330 is preferably mechanically coupled to printhead 214 so that the position controller 312 simultaneously moves the sensor 330 and the printhead 214.

Figure 4A:
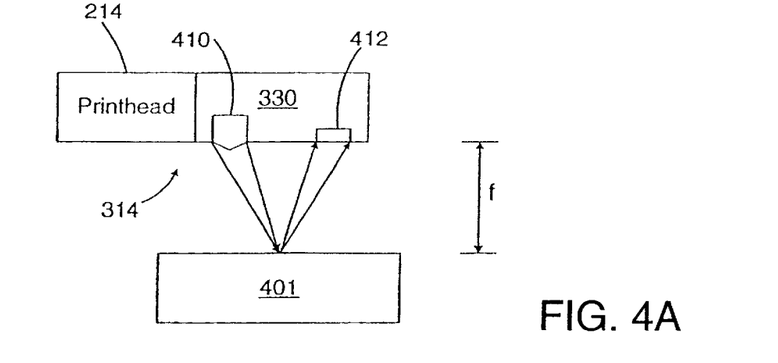
FIGS. 4A and 4B show one embodiment of a printhead-sensor constructed according to the invention separated from a reflective surface by a distance that is within and outside of, respectively, the detection range of the proximity sensor.
Figure 4B:
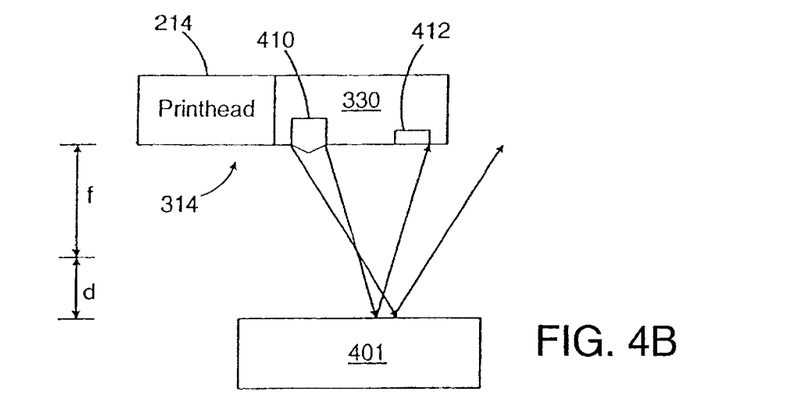

FIGS. 4A and 4B illustrate one embodiment of a printhead-sensor 314 constructed according to the invention. It will be appreciated that FIGS. 4A and 4B (as well as the other drawings of this application) are not drawn to scale, and the sensor 330 is generally much smaller than the printhead 214. In this embodiment, sensor 330 is implemented as a reflective sensor. As shown, sensor 330 includes a light emitting element 410 disposed a fixed distance away from a photosensitive detector 412. The light emitting element 410 is configured so that all light emitted by the element 410 is focused on a spot that is (1) a vertical distance f away from the sensor 330 and (2) offset from the element 410. FIG. 4A shows printhead-sensor 314 disposed a distance f away from a reflective object 401. As shown, light emitted by element 410 is reflected by the upper surface of object 401 and this reflected light is received by detector 412. FIG. 4B shows printhead-sensor 314 disposed a distance f+d away from object 401. As shown, the additional separation between the object 401 and the printhead-sensor 314 of the distance d prevents the detector 412 from receiving any of the light emitted by element 410.

Sensor 330 may be used as a proximity detector. Detector 412 will only receive light from element 410 when the sensor 330 is disposed a distance f plus or minus some delta away from a reflective surface. If the sensor is separated from an object by some other distance, the detector 412 will not receive any light from element 410. So, when detector 412 receives light from element 410, it may be concluded that the printhead-sensor 314 is separated from an object by a particular distance. Reflective sensors of this type are well known and are sometimes called "reflective type photo-interrupters". The GP2A20, which is sold by Sharp Microelectronics Group of Carnas, Wash., is an example of a commercially available version of this type of sensor. Other examples of such sensors are the Omron EE-SB5 series sold by Omron Electronics, Inc., of Schaumberg, Ill., and the Keyence PZ series sold by Keyence Corp. of America, of Woodbridge, N.J. Such sensors are typically configured so that they will detect the presence of objects that are separated from the sensor by three to seven millimeters and will not detect objects that are further away.

Figure 5A:
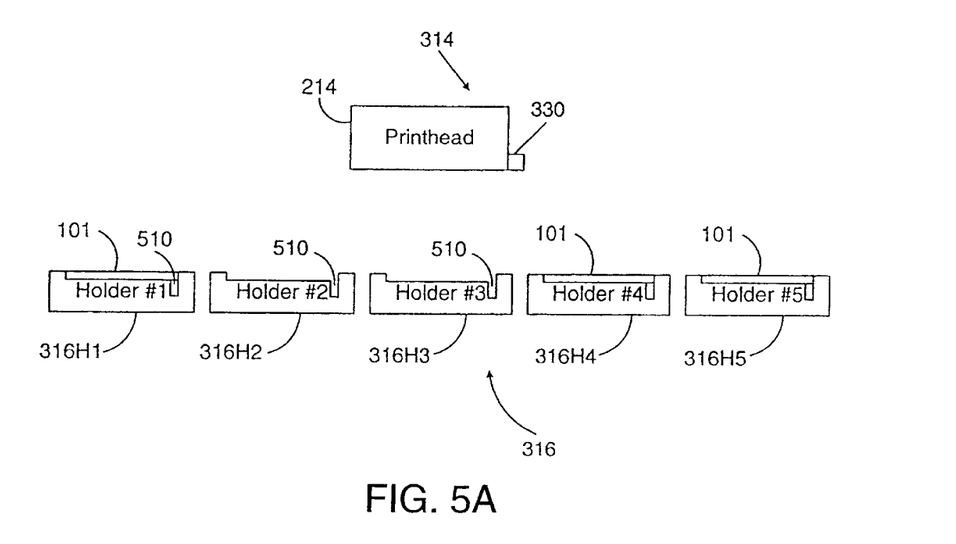
FIG. 5A shows the printhead-sensor illustrated in FIGS. 4A and 4B disposed over a substrate station of a spotting instrument constructed according to the invention.

FIG. 5A illustrates how an embodiment of printhead-sensor 314 that includes a reflective sensor 330 of the type shown in FIGS. 4A and 4B may be used in accordance with the invention to detect the presence or absence of substrates in substrate station 316. The illustrated substrate station 316 includes five platforms or holders 316H1, 316H2, 316H3, 316H4, 316H5, for holding substrates. Microarray substrates 101 are mounted in three of the five holders, 316H1, 316H4, 316H5 and the remaining holders 316H2, 316H3 are empty, or unoccupied by a substrate. It will be appreciated that substrate stations used in spotting instruments constructed according to the invention may include many more holders for holding additional substrates; however, for convenience of illustration, only five holders are shown. Each of the holders in substrate station 316 defines a receiving area for holding a substrate and a well 510 disposed in the receiving area underneath where a substrate would be disposed if a substrate were mounted in the holder. For example, as illustrated, the substrate 101 in holder 316H1 covers the well 510, and in holder 316H2, in which no substrate is mounted, the well 510 is exposed or uncovered. It will be appreciated that the well 510 could be located in other positions than as illustrated in FIG. 5A. For example, while FIG. 5A shows the well 510 as positioned in the receiving area so as to be located underneath the outer perimeter of a substrate mounted in the holder, the well could be alternatively located under the center of a mounted substrate.

In operation, instrument 300 detects whether a substrate is mounted in one of the holders by positioning the sensor 330 of printhead-sensor 314 a selected distance away from the holder over the well 510. The distance is selected so that if a substrate is mounted in a particular holder, the sensor 330 will be spaced apart from the substrate by a distance that is within the detection range of the sensor. If a substrate 101 is present in the holder, light emitted from the sensor's light emitting element 410 will be reflected by the substrate and detected by the detector 412. Alternatively, if no substrate is present, light emitted by the light emitting element 410 will travel into the well 510 and will not be reflected towards the detector 412. The well 510 is preferably sized to insure that light entering the well will not be reflected towards the detector. One good choice for the well dimensions is about seven millimeters deep and about nineteen millimeters wide. Such wells will work well with sensors 330 that are optimized for detecting objects that are spaced apart from the sensor by three to seven millimeters away such as the above-referenced GP2A20 sensor. So, instrument 300 can use printhead-sensor 314 to detect whether a substrate is mounted in any of the holders of substrate station 316.

It is important to be able to place the sensor 330 close enough (e.g., within four millimeters) to a substrate so that the sensor 330 can detect the presence or absence of the substrate without causing other structures of the spotting apparatus, such as pins mounted in the printhead, to contact the substrate. Although FIG. 5A, as well as other drawings in the present application, illustrate sensor 330 as being disposed adjacent to the bottom of printhead 214, it will be appreciated that a bracket or other type of mounting device may be used to attach sensor 330 to printhead 214 and the bracket may locate sensor 330 above, below, or at a selected location with respect to the printhead. For example, no pins are shown as being mounted in printhead 214 in FIG. 5A. If printhead 214 was of the pin-type, and pins were mounted within the printhead, the pin shafts would extend below the printhead as illustrated for example in FIG. 1F. In such a case, it could be advantageous to use a bracket to mount the sensor 330 to the printhead 214 so that the sensor 330 would be disposed below the bottom of the printhead 214. This would permit the printhead sensor 314 to be moved so as to place the sensor 330 close enough to a substrate so as to detect the substrate without causing the pins to contact the substrate. It will be appreciated that all sensors discussed herein could be mounted or connected to the printhead so as to selectively control the vertical distance between the sensor and the bottom of the printhead.

Prior art spotting instruments generally assumed that microarray substrates were mounted in all holders of the substrate station. Alternatively, if any holders were known to be empty, a human operator had to provide that information to the instrument. In general, attempting to print spots onto a substrate of an empty holder results in either damage to the spotting instrument (e.g., by causing unwanted contact between pins of a pin-type instrument with the empty holder) or in waste of target material (e.g., because jets of a jet-type instrument may emit target material over the empty holder). Also, since a single run of a spotting instrument generally takes many hours, prior art spotting instruments typically had to rely on information that was many hours old during the run. For example, a human operator may correctly indicate to the instrument that microarray substrates are mounted in all holders of the substrate station at the beginning of a run. However, if one of the substrates becomes inadvertently dislodged during the run, such information would not typically be reported to the instrument unless the human operator fortuitously happened to discover the condition during the run.

Instead of relying on a human operator to provide information regarding the state of the substrate station, spotting instrument 300 may advantageously use printhead-sensor 314 to accurately determine whether a microarray substrate is mounted within any of the holders of substrate station 316 at any time. Spotting instrument 300 thereby advantageously minimizes the risk of damaging the instrument during a run and also advantageously minimizes waste of target material.

In one preferred mode of operation of spotting instrument 300, the processor 310 uses the printhead-sensor 314 to determine whether a microarray substrate is mounted within a holder of substrate station 316 immediately prior to using the printhead-sensor 314 to print spots onto that substrate. If instrument 300 detects that a substrate is present or mounted in a particular holder, then the instrument prints a pattern of spots onto that substrate. Alternatively, if instrument 300 detects that a substrate is not present, then the instrument moves on to the next holder of substrate station 316 without attempting to print spots onto a substrate of the empty holder. Once instrument 300 determines that a particular holder is empty, the instrument may avoid returning the printhead-sensor to that holder for the duration of the run. Alternatively, upon detection of an empty holder, the instrument 300 may indicate an error condition. If this error condition is later reset, for example either by a human operator or automatically by actions of the substrate station, the instrument may continue to print spots on the substrate mounted in that holder.

Since instrument 300 is capable of detecting whether a substrate is present immediately before printing spots onto that substrate, instrument 300 minimizes the risk that conditions will change between the detection of whether a holder is empty and the printing of spots onto a substrate of that holder. In this regard, sensor 330 is preferably physically coupled to printhead 214 so the instrument 300 may use the sensor 330 to detect whether a holder is empty immediately before using the printhead to print spots onto a substrate in that holder. Also, physically coupling the sensor to the printhead allows a single position controller to control movements of both the sensor and the printhead. It will be appreciated however that in other embodiments the printhead and the sensor may be mechanically separable and capable of independent movement.

Figure 5B:
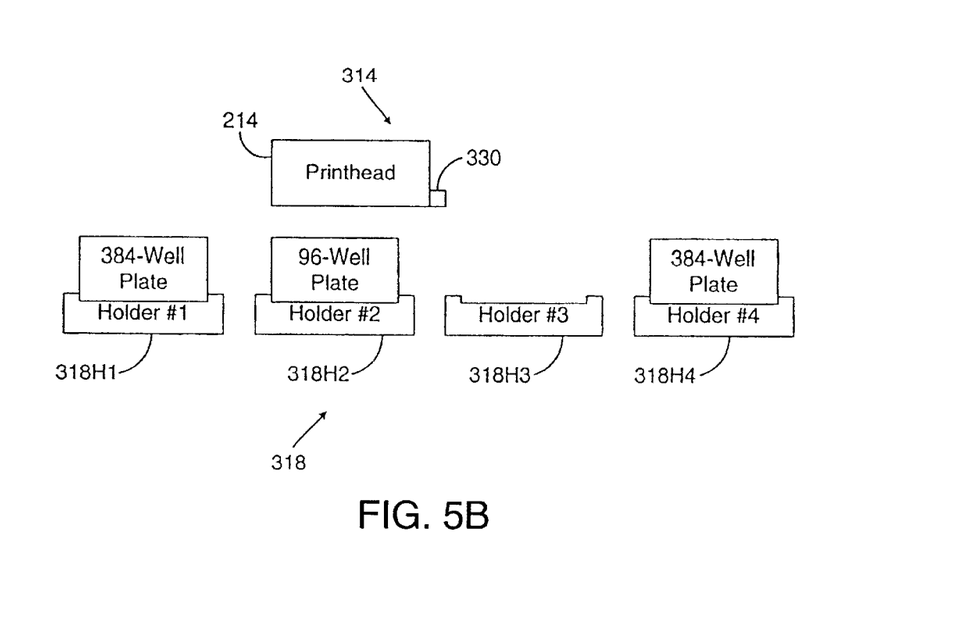
FIG. 5B shows the printhead-sensor illustrated in FIGS. 4A and 4B disposed over a well station of a spotting instrument constructed according to the invention.

FIG. 5B shows how an embodiment of printhead-sensor 314 that includes a reflective sensor 330 of the type shown in FIGS. 4A and 4B may be used in accordance with the invention to detect the presence or absence of reservoirs in well station 318. The illustrated well station 318 includes four platforms or holders 318H1, 318H2, 318H3, 318H4, for holding reservoirs of target material. Plates are mounted in three of the four holders, 318H1, 318H2, 318H4 and the remaining holder 318H3 is empty, or unoccupied by a plate.

It will be appreciated that well stations used in spotting instruments constructed according to the invention may include many more holders for holding wells; however, for convenience of illustration, only four holders are shown.

In operation, instrument 300 detects whether a reservoir is mounted in one of the holders by positioning the sensor 330 of printhead-sensor 314 over the holder so that if a reservoir were mounted in the holder the sensor 330 would be spaced apart from the reservoir's upper surface by a distance within the detection range of sensor 330 (e.g., four to seven millimeters if the sensor 330 is implemented using the above-referenced GP2A20). If a reservoir is present in the holder, light emitted from the sensor's light emitting element 410 will be reflected by the reservoir and detected by the detector 412. Alternatively, if no reservoir is present, light emitted by the light emitting element 410 will travel toward the holder and will not be received by detector 412. So, instrument 300 can use printhead-sensor 314 to detect whether a reservoir is mounted within any of the holders of well station 318.

In addition to detecting whether a reservoir is mounted within a holder of well station 318, instrument 300 can also use sensor 330 to detect the type of reservoir that is mounted within a holder. For example, if instrument 300 detects that a reservoir is mounted within a particular holder of well station 318, instrument 300 may then use sensor 330 to detect whether the reservoir is a 96-well plate, a 384-well plate, or some other type of plate (e.g., a 1536-well plate).

Figure 6:
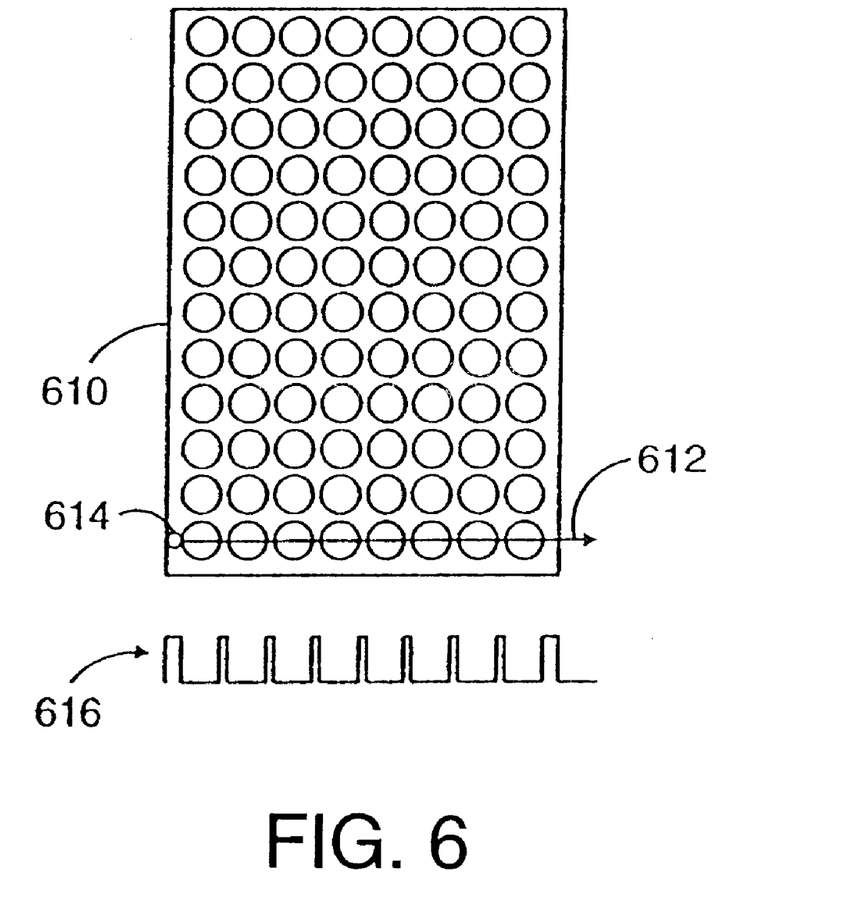
FIG. 6 shows a trajectory that may be taken by the printhead-sensor shown in FIGS. 4A and 4B over a 96-well plate and a graph illustrating the response of the sensor while traveling along that trajectory.

FIG. 6 illustrates an example of how instrument 300 may use sensor 330 to detect the type of plate mounted in a holder of well station 318. FIG. 6 shows a 96-well plate 610, and the arrow 612 drawn across the plate represents a trajectory of the sensor 330. Initially, processor 310 of instrument 300 would direct position controller 312 to position the sensor 330 of printhead-sensor 314 over the circle shown 614 at the extreme left of the arrow in FIG. 6. In this position, the processor 310 can use the sensor 330 to detect whether a reservoir is present in the holder. After confirming that some type of reservoir is present, the processor 310 can direct the position controller 312 to move the printhead-sensor 314 so that the sensor 330 moves along the trajectory illustrated by the arrow 612. The graph 616 drawn below the 96-well plate 610 illustrates the response of the sensor 330 as the sensor is moved along the trajectory illustrated by the arrow 612. As indicated by the graph 616, when the sensor 330 is positioned over the wells of the 96-well plate, the sensor 330 will not detect the presence of an object (the absence of an object being illustrated by the lower level in the graph of FIG. 6) because the bottom of the wells are beyond the sensor's detection range. When the sensor 330 is positioned over the upper surface of the 96-well plate (e.g., in the spaces between the wells), the sensor 330 will detect the presence of an object. So, while traveling along the trajectory indicated by arrow 612, the sensor 330 will periodically detect the presence of an object, each detection being indicated by one of the spikes in the graph 616 of FIG. 6. Processor 310 may determine the type of reservoir in the holder by measuring the frequency (or number) of the detections, or spikes. For any given speed of movement of the printhead-sensor 314, the frequency of detections will be four times greater for 384-well plates than for 96-well plates. Other frequencies will be indicative of other types of plates. It will be appreciated that other trajectories could be followed to detect or distinguish between other types of plates.

As with substrates, prior art spotting instruments had to rely upon human operators to insure that all necessary reservoirs of target material were mounted within the well station. Errors in this regard sometimes led to damage of the spotting instrument. For example, in a pin-type instrument, pins that are intended to be dipped into a 384-well plate are spaced apart from one another by 4.5 mm. If the spotting instrument erroneously attempted to dip these pins into a 96-well plate (in which the well centers are separated by 9.0 mm), damage to the pins could result. Human error regarding locations of wells in the well station also led to fabrication errors in the production of microarrays (e.g., spots could be formed on the substrates using the wrong target material).

Rather than relying on human input, spotting instrument 300 can advantageously, automatically determine whether a plate is mounted within a particular holder of well station 318 immediately prior to directing the printhead 214 to collect a sample of target material from that plate. Also, if the presence of a plate is detected, spotting instrument 300 can advantageously automatically determine the type of plate that is so mounted before directing the printhead 214 to collect a sample of target material from that plate.

In operation of instrument 300, processor 310 preferably uses printhead-sensor 314 to detect whether a reservoir is mounted in a holder of well station 318 immediately before attempting to collect a sample of target material from that reservoir. If instrument 300 unexpectedly detects that a particular holder of the well station is empty, the instrument 300 may stop printing and indicate an error condition. Alternatively, the instrument could set an error flag indicating that the holder is empty and continue printing using other reservoirs. In this case, manual actions of a human operator or automatic actions of the well station 318 may be able load the empty holder with the necessary reservoir before the instrument finishes printing spots associated with other reservoirs. This advantageously allows problems such as empty holders in the well station 318 to be solved without delaying the process of producing microarrays.

If instrument 300 detects that a plate is mounted in a holder of the well station 318, instrument 300 may also advantageously use printhead-sensor 314 to verify that the type of plate present matches the type of plate expected. For example, if the processor 310 expects a 384-well plate to be mounted in a particular holder, the processor 310 may use printhead-sensor 314 to verify that the plate mounted in the holder is actually a 384-well plate. If the type of plate detected matches the type of plate that the processor expected, printing can continue. However, if the type of plate detected does not match the type of plate expected, an error flag may be set and production of microarrays may continue using plates mounted in other well stations. This error may be rectified as discussed above either by manual or automatic actions of a human operator or the well station.

Figure 7A:
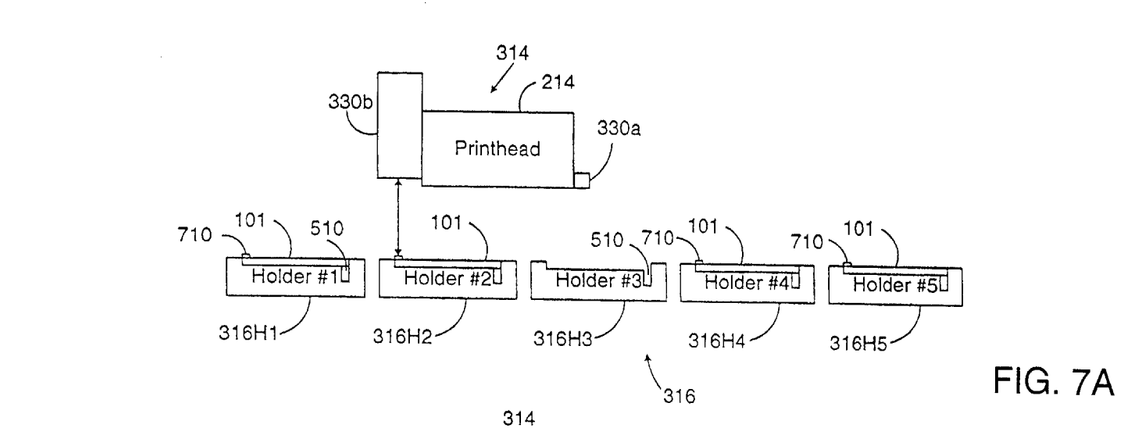
FIG. 7A shows an other embodiment of a printhead-sensor constructed according to the invention disposed over a substrate station of a spotting instrument constructed according to the invention.
Figure 7B:
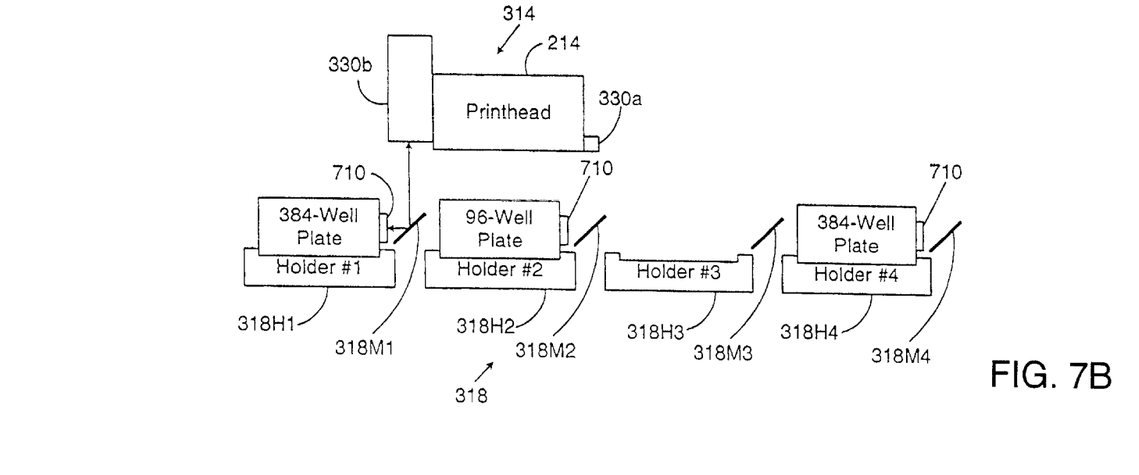
FIG. 7B shows the printhead-sensor of FIG. 7A disposed over a well station of a spotting instrument constructed according to the invention.

FIGS. 7A and 7B illustrate another embodiment of a printhead-sensor 314 constructed according to the invention and how that printhead-sensor may be used to discern information about substrates and plates mounted in the spotting instrument 300. In this embodiment, the printhead-sensor 314 includes two sensors 330a, 330b. Sensor 330a is a reflective sensor of the type discussed above and illustrated in FIGS. 4A and 4B. Sensor 330b is a bar code reader. Reflective sensor 330a and bar code reader 330b are affixed to opposite ends of the printhead 214. Bar code reader 330b is preferably disposed so that its optical elements face downwards and so that light emitted by reader 330b travels downwards as illustrated by the arrows in FIGS. 7A and 7B. In addition to detecting the presence of absence of substrates or plates in the spotting instrument 300, bar code reader 330b can advantageously determine the specific identity of each substrate and plate mounted in the spotting instrument 300. Bar code reader 330b may be implemented, for example, using a Keyence BL-500H or Keyence BL-600H bar code reader, which are sold by Keyence Corp. of America, of Woodbridge, N.J., or by using an Omron V550-A20HD bar code reader, which is sold by Omron Electronics, Inc., of Schaumberg, Ill.

FIG. 7A shows printhead-sensor 314 disposed over substrate station 316 of instrument 300. Preferably, a high resolution bar code label 710 is affixed to the upper surface of each substrate loaded into instrument 300. These bar code labels 710 can be of the same variety used to label microarray substrates for microarray scanning instruments. For example, these bar code labels are relatively small and are ordinarily rectangular and measure about 0.9 inches by 0.55 inches. By positioning the bar code reader 330b of printhead-sensor 314 over the bar code label 710 of one of the substrates, instrument 300 can read the bar code label 710 and thereby specifically and uniquely identify the substrate.

If bar code labels 710 are included on the upper surface of plates loaded into the well station 318, instrument 300 can similarly use the bar code reader 330b of printhead-sensor 314 to read the bar code labels and thereby specifically identify the plates. However, as discussed above, a convention has already developed for placing bar code labels on the sides of plates as illustrated in FIG. 7B. FIG. 7B shows an embodiment of well station 318 constructed according to the invention that allows printhead-sensor 314 to read bar code labels that have been fixed to the sides of plates in accordance with the prior art convention. Well station 318 includes a plurality of mirrors, or reflective surfaces 318M. One of these mirrors is disposed adjacent to each of the holders 318H in well station 318. The mirrors 318M allow downward looking bar code reader 330b to inspect the bar code labels 710 on the sides of any of the plates in well station 318 while the printhead-sensor 314 is disposed above the well station 318. For example, as shown in FIG. 7B, the mirror 318M1 allows downward looking bar code sensor 330b to inspect the bar code label 710 on the plate mounted in the holder 318H1. Since the surfaces of the plates onto which the bar code labels 710 are affixed are parallel to the direction of focus for the bar code reader 330b, the bar code reader 330b would ordinarily not be able to inspect the bar code labels. However, the mirrors 318M are positioned to redirect the light emitted by the bar code reader 330b toward the bar code labels, and to redirect the light reflected by the bar code labels 710 back towards the bar code reader 330b. The mirrors 318M are preferably angled at forty five degrees with respect to the holders as illustrated in FIG. 7B, although it will be appreciated that other angles would function as well. It will be appreciated that since the sides of the plates are relatively large, the bar code labels affixed to the sides of plates need not be of the high resolution type used for substrates. Accordingly, bar code reader 330b is preferably capable of reading both high resolution and low resolution labels.

Including bar code reader 330b in printhead-sensor 314 adds significant capability to spotting instrument 300. For example, bar code reader 330b permits instrument 300 to generate a record (or data base) that specifies the identity of every spot of every microarray produced by instrument 300. In operation of instrument 300, processor 310 may use bar code reader 330b to read the bar code label on a plate in well station 318 before collecting samples of target material from that plate. Similarly, processor 310 may use bar code reader 330b to read the bar code label on a substrate in substrate station 316 before printing spots onto that substrate. Knowing the identity of every plate from which samples of target material are collected and knowing the identity of every substrate onto which spots are printed allows instrument 300 to accurately record the configuration of every microarray produced by instrument 300.

In one preferred mode of operation, the identity of all plates to be used for production of a batch of microarrays is input to the spotting instrument 300. After using bar code reader 330*b* to read the label of a particular plate, processor 310 may determine whether that plate should be used for production of the current batch of microarrays, and of so, which spots should be printed using samples from that plate. If the processor 310 determines that a particular plate mounted in the well station should not be used in the current run, the instrument may continue printing using samples from other plates. The instrument may also indicate an error condition.

Another mode of operation for instrument 300 is to program processor 310 in terms of the holders of well station 318 without reference to bar code labels of particular plates. In this mode, the instrument 300 is instructed that certain spots should be printed using a plate in the first holder, certain spots should be printed using plates in the second holder, and so on. This mode is similar to modes of operation of prior art spotting instruments. As with the prior art, in this mode, the desired microarrays will only be produced if the plates are properly distributed throughout the well station. However, this mode is distinct from the prior art because in this mode the instrument reads the bar code label of each plate before acquiring samples from that plate and generates a record relating the bar code label of the plate to the spots printed with samples from that plate. In the prior art, if plates were improperly ordered in the well station, or if the wrong plates were located in the well station, it was extremely difficult to subsequently analyze the completed microarray. However, in this mode, a record is generated while the microarray is being fabricated that relates every spot on the microarray to a bar code label of a particular plate. This record may be subsequently analyzed to determine the configuration of the microarray. It will be appreciated that many other modes of operation for instrument 300 are possible and are encompassed within the invention.

In many cases, bar code reader 330*b* may eliminate the need for reflective sensor 330*a*. For example, if bar code reader 330*b* successfully reads a bar code label from a plate in a holder of well station 318, it may be unnecessary to use reflective sensor 330*a* to confirm that a plate is mounted that holder and the same is true for substrates. However, the preferred embodiment of printhead-sensor 314 includes both a bar code reader 330*b* and a reflective sensor 330*a*. Including both types of sensors provides maximum flexibility and allows instrument 300 to operate with plates and substrates regardless of whether they include bar code labels. Also, even if bar code reader 330*b* reads a bar code label from a plate or substrate, it may still be advantageous to use sensor 330*a* to confirm that the plate or substrate is properly mounted in its holder. Since sensor 330*a* generally provides more accurate information regarding the physical position of an object, sensor 330*a* may be more reliable than bar code reader 330*b* for determining whether a plate or substrate is properly mounted. Also, sensor 330*a* will function even if no bar code labels are included on the substrates or plates. It will be appreciated however that printhead-sensors may be constructed according to the invention using only one of the two sensors (i.e., either the bar code reader or the reflective sensor). Moreover, other types of proximity detectors (e.g., ultrasonic transducers) may be substituted for reflective sensor 330*a*, and other types of sensors for reading machine readable indicia, markings, or labels may be substituted for bar code reader 330*b*.

In other embodiments of spotting instruments constructed according to the invention, instead of fixing one or two sensors to the printhead, a plurality of sensors could be included in the substrate and well stations. For example, one bar code reader could be included for each holder in the well and substrate stations. However, for several reasons it is preferred to mechanically fix the sensors to the printhead as discussed above. For example, fixing the sensors to the printhead eliminates the need for using multiple sensors throughout the well and substrate stations. Also, fixing the sensors to the printhead allows a single position controller to manipulate or move both the printhead and the sensors and thereby eliminates the need for extra position controllers. Further, the range of motion needed for the printhead-sensor to detect the presence of plates or substrates or to read bar code labels is very similar to the range of motion provided to printheads in a prior art spotting instruments. So, only minor modifications to a prior art instrument are necessary to obtain the benefits of the invention.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. An apparatus for producing a microarray, including:
   (A) a first holder for holding a substrate;
   (B) a second holder for holding a reservoir of target material;
   (C) a device for transferring some target material from a reservoir located in the second holder to a selected location on a substrate located in the first holder; and
   (D) a detector for detecting whether a substrate is located in the first holder and for detecting whether a reservoir is located in the second holder.

2. An apparatus according to claim 1, wherein the detector comprises an optical detector.

3. An apparatus according to claim 1, wherein the detector comprises a reflective sensor.

4. An apparatus according to claim 1, wherein the detector comprises a proximity detector.

5. An apparatus according to claim 1, wherein the detector is coupled to the device.

6. An apparatus according to claim 1, the device and detector being movable.

7. An apparatus according to claim 1, wherein the detector comprises a bar code reader.

8. An apparatus according to claim 7, further including a mirror for reflecting light from the bar code reader towards the second holder.

9. An apparatus according to claim 1, wherein the device comprises a printhead.

10. An apparatus according to claim 1, wherein the device comprises a pin-type printhead.

11. An apparatus according to claim 1, wherein the device comprises a jet-type printhead.

12. An apparatus according to claim 1, wherein the detector detects whether a substrate is located in the first holder when the device is positioned proximal to the first holder, and the detector detects whether a reservoir is located in the second holder when the device is positioned proximal to the second holder.

13. An apparatus for producing a microarray, including:
(A) a first holder for holding a substrate;
(B) a second holder for holding a reservoir of target material;
(C) a device for transferring some target material from a reservoir located in the second holder to a selected location on a substrate located in the first holder; and
(D) a detector for detecting whether a substrate is located in the first holder.

14. An apparatus for producing a microarray, including:
(A) a first holder for holding a substrate;
(B) a second holder for holding a reservoir of target material;
(C) a device for transferring some target material from a reservoir located in the second holder to a selected location on a substrate located in the first holder; and
(D) a detector for detecting whether a reservoir is located in the second holder.

15. A method of producing a microarray, comprising:
(A) providing a first holder for holding a substrate;
(B) providing a second holder for holding a reservoir of target material;
(C) providing a device for collecting some target material from a reservoir located in the second holder and for placing at least some of the collected target material at a selected location on a substrate located in the first holder; and
(D) detecting whether a reservoir is located in the second holder before attempting to collect target material from the reservoir.

16. A method according to claim 15, further comprising detecting whether a substrate is located in the first holder before attempting to place target material on the substrate.

17. A method of producing a microarray, comprising:
(A) providing a first holder for holding a substrate;
(B) providing a second holder for holding a reservoir of target material;
(C) providing a device for collecting some target material from a reservoir located in the second holder and for placing at least some of the collected target material at a selected location on a substrate located in the first holder; and
(D) detecting whether a substrate is located in the first holder before attempting to place target material on the substrate.

18. A method according to claim 17, further comprising detecting whether a reservoir is located in the second holder before attempting to collect target material from the reservoir.

* * * * *